United States Patent
Burton et al.

(10) Patent No.: US 9,066,749 B2
(45) Date of Patent: Jun. 30, 2015

(54) CUTTING OR SCORING BALLOON AND APPARATUS THEREFOR

(71) Applicant: Cook Medical Technologies LLC, Bloomington, IN (US)

(72) Inventors: David G. Burton, Bloomington, IN (US); Per Elgaard, Haslev (DK)

(73) Assignee: Cook Medical Technologies LLC, Bloomington, IN (US)

(*) Notice: Subject to any disclaimer, the term of this patent is extended or adjusted under 35 U.S.C. 154(b) by 0 days.

(21) Appl. No.: 13/803,987

(22) Filed: Mar. 14, 2013

(65) Prior Publication Data

US 2014/0088624 A1 Mar. 27, 2014

(30) Foreign Application Priority Data

Sep. 24, 2012 (GB) .................................. 1216965.2

(51) Int. Cl.
*A61B 17/3207* (2006.01)
*A61M 25/10* (2013.01)
*A61B 17/22* (2006.01)

(52) U.S. Cl.
CPC ......... *A61B 17/320725* (2013.01); *Y10T 29/49* (2015.01); *A61M 25/1002* (2013.01); *A61M 25/1038* (2013.01); *A61M 2025/1004* (2013.01); *A61M 2025/1086* (2013.01); *A61B 2017/22061* (2013.01)

(58) Field of Classification Search
CPC .............. A61B 2017/22051; A61B 17/12022; A61B 2017/22001; A61B 17/320725; A61M 2025/109; A61M 25/104; A61M 25/10
USPC ................. 606/159, 170, 192, 167, 180, 70; 604/103.14, 103.8, 96.01, 103.7, 271, 604/103.08; 425/392; 264/198
See application file for complete search history.

(56) References Cited

U.S. PATENT DOCUMENTS

| | | | |
|---|---|---|---|
| 5,030,201 A | 7/1991 | Palestrant | |
| 5,209,799 A | 5/1993 | Vigil | |
| 6,988,881 B2 * | 1/2006 | Motsenbocker et al. | 425/392 |
| 7,270,673 B2 * | 9/2007 | Yee et al. | 606/159 |
| 7,407,377 B2 | 8/2008 | Motsenbocker et al. | |
| 7,413,558 B2 | 8/2008 | Kelley et al. | |
| 7,618,252 B1 * | 11/2009 | Goff | 425/392 |
| 7,762,804 B1 | 7/2010 | Stupecky | |
| 7,976,557 B2 * | 7/2011 | Kunis | 606/159 |
| 2004/0034384 A1 * | 2/2004 | Fukaya | 606/191 |
| 2005/0251194 A1 | 11/2005 | McHale | |

(Continued)

FOREIGN PATENT DOCUMENTS

WO WO 2006/073993 A2 7/2006

OTHER PUBLICATIONS

Extended Search Report for European Patent Application Serial No. 13176086.0 dated Mar. 4, 2015, 7 pages.

*Primary Examiner* — Katrina Stransky
*Assistant Examiner* — Mikail Mannan
(74) *Attorney, Agent, or Firm* — Brinks Gilson & Lione

(57) ABSTRACT

A cutting or scoring balloon (26) is provided with a plurality of cutting or scoring elements (34) and is wrapped onto a balloon catheter (12) such that the cutting or scoring elements (34) overlie the balloon wall (36) with the balloon wall (36) pleated underneath the cutting or scoring elements (34). The cutting or scoring elements (34) remain exposed when the balloon (26) is pleated and wrapped onto the balloon catheter (12) and in a tightly wrapped configuration.

9 Claims, 6 Drawing Sheets

(56) References Cited

U.S. PATENT DOCUMENTS

| | | |
|---|---|---|
| 2007/0129748 A1 | 6/2007 | Eidenschink et al. |
| 2009/0234283 A1* | 9/2009 | Burton et al. ............ 604/103.08 |
| 2011/0160756 A1* | 6/2011 | Aggerholm et al. .......... 606/159 |

\* cited by examiner

CUTTING OR SCORING BALLOON AND APPARATUS THEREFOR

This application claims the benefit of the filing date of United Kingdom (GB) patent application number 1216965.2, filed Sep. 24, 2012, which is hereby incorporated by reference herein.

TECHNICAL FIELD

The present invention relates to a cutting or scoring balloon and to apparatus for and a method of pleating and wrapping such a balloon.

BACKGROUND OF THE INVENTION

Cutting or scoring balloons are known for opening occluded or constricted vessels of a patient, caused for instance by stenosis. Such balloons may have one or more blades or cutting elements fixed to or otherwise integral with the balloon wall, used for cutting or fragmenting stenosed material from the vessel wall. These balloons are generally effective in opening stenosed vessels. However, difficulties arise with the deployment of such balloons as a result of the risk of the balloon wall being cut or torn by the cutting or scoring elements. As a result, these balloons tend to be wrapped in such a manner that the balloon wall is kept away from the cutting or scoring elements when the balloon is in a deflated state. This may be by a particular balloon folding arrangement or by provision of a protective wrapping around the cutting or scoring elements. Whilst these methods may be effective in reducing the risk of damage to the balloon wall, they lead to a balloon which is loosely wrapped and which thus has a much greater delivery footprint (diameter) than simple medical balloons which are tightly wrapped onto the balloon catheter. A wider introducer assembly is harder to deploy endoluminally in a patient. Moreover, a balloon which has a greater deflated diameter is not suitable to treating heavily stenosed vessels, that is having only a small opening through the stenosed area, or for treating smaller diameter vessels.

Examples of prior art cutting or scoring balloons can be found for instance in U.S. Pat. No. 7,413,558 and U.S. Pat. No. 5,209,799. Apparatus for folding or wrapping standard balloon catheters can be seen, for example, in U.S. Pat. No. 7,762,804, U.S. Pat. No. 5,209,799, U.S. Pat. No. 7,618,252 and US-2005/0251194.

SUMMARY OF THE INVENTION

The present invention seeks to provide an improved cutting or scoring balloon and improved apparatus for and method of pleating and wrapping a cutting or scoring balloon.

According to an aspect of the present invention, there is provided a pleated or wrapped cutting or scoring balloon, the balloon including a flexible balloon wall having inner and outer surfaces, the balloon wall providing a balloon body portion extending along a longitudinal axis of the balloon and having a circumferential periphery; and a plurality of cutting or scoring elements integral with or attached to the outer surface of the balloon wall, said cutting or scoring elements extending substantially along said longitudinal axis and being spaced from one another along the circumferential periphery of the body portion; wherein balloon wall located between the cutting or scoring elements is wrapped underneath the cutting or scoring elements such that the cutting or scoring elements are exposed on the wrapped balloon.

Such a balloon arrangement represents a departure from the art by keeping the cutting or scoring elements exposed even when the balloon is in a folded or fully wrapped configuration. There is no risk of damage to the balloon wall by the cutting or scoring elements as the balloon wall is pleated and wrapped under these elements. It is thus possible to achieve a much tighter wrapped balloon structure able to be deployed in smaller lumens and through narrower stenosed regions than prior art devices. A tighter wrapping also enhances trackability and pushability of the introducer assembly used for deploying the balloon.

In addition, this pleating and wrapping arrangement leaves the cutting or scoring elements exposed even when the balloon is tightly wrapped on its balloon catheter. This thus enables the cutting or scoring elements to perform their function at all states of the balloon, that is when it is fully wrapped, as it is inflating and when it is fully inflated. This contrasts with prior art arrangements which provide protection around the cutting or scoring elements until the balloon is inflated.

It will be appreciated that the cutting or scoring balloon will in practice be disposed on and fixed to a balloon catheter, as is known in the art.

In an embodiment, a first part of the balloon wall between the cutting or scoring elements is pleated and wrapped underneath the cutting or scoring element and a second part of said balloon wall is pleated and wrapped to one side of said cutting or scoring element. This second part preferably extends circumferentially around the pleated and wrapped balloon to a rotational position short of an adjacent cutting or scoring element. Thus, it is not necessary for the entirety of the pleated and wrapped balloon wall to be located underneath the cutting or scoring elements, as a part of the pleated and wrapped structure may extend towards an adjacent cutting or scoring element but end radially before this so as not to risk being damaged thereby.

The cutting or scoring elements are integral with the balloon wall and/or attached to the balloon wall. In other words, the teachings herein apply to all types of cutting and scoring elements, including elements formed integrally with the balloon wall, for instance as ribs of thicker material, and elements attached to the balloon wall, such as cutting blades, wires and so on.

According to another aspect of the present invention, there is proved a method of pleating a cutting or scoring balloon, the balloon including a flexible balloon wall having inner and outer surfaces, the balloon wall providing a balloon body portion extending along a longitudinal axis of the balloon and having a circumferential periphery; and a plurality of cutting or scoring elements on or attached to the outer surface of the balloon wall, said cutting or scoring elements extending substantially along said longitudinal axis and being spaced from one another along the circumferential periphery of the body portion; the method including the step of pleating balloon wall located between the cutting or scoring elements underneath the cutting or scoring elements such that the cutting or scoring elements are exposed on the pleated balloon. The balloon is preferably tightly wrapped.

According to another aspect of the present invention, there is provided apparatus for pleating a cutting or scoring balloon, which balloon is provided with a flexible balloon wall having inner and outer surfaces, the balloon wall providing a balloon body portion extending along a longitudinal axis of the balloon and having a circumferential periphery; and a plurality of cutting or scoring elements on or attached to the outer surface of the balloon wall, said cutting or scoring elements extending substantially along said longitudinal axis and being spaced from one another along the circumferential periphery of the body portion; the pleating and wrapping apparatus including a plurality of pleating elements arranged in facing relationship with one another, said pleating elements being movable from an open position in which the blades provide a passage for an unfolded balloon and a closed position in which the pleating elements are close to or adjacent one another; each of said pleating elements including an elongate pleating blade and first and second pleating surfaces either side of the blade; wherein the first pleating surface of one pleating element faces the second pleating surface of an adjacent pleating element; wherein facing first and second pleating surfaces in the closed position of the pleating elements provide a gap therebetween for holding a cutting or scoring element of the balloon with balloon wall pleated underneath the cutting or scoring element.

Preferably, the first and second pleating surfaces are circumferentially curved.

Facing first and second pleating surfaces preferably provide a space for receiving and pleating a portion of balloon wall.

In the preferred embodiment, there is provided a balloon feed mechanism operable to provide for feeding and rotation of a balloon into the pleating elements.

Advantageously, the apparatus includes a wrapping device provided with circumferentially constricting tightening elements which compress the pleated balloon into a tightly wrapped condition.

According to another aspect of the present invention, there is proved a method of pleating a cutting or scoring balloon provided with a flexible balloon wall having inner and outer surfaces, the balloon wall providing a balloon body portion extending along a longitudinal axis of the balloon and having a circumferential periphery; and a plurality of cutting or scoring elements on or attached to the outer surface of the balloon wall, said cutting or scoring elements extending substantially along said longitudinal axis and being spaced from one another along the circumferential periphery of the body portion; the method using pleating apparatus including a plurality of pleating elements arranged in facing relationship with one another, said pleating elements being movable from an open position in which the blades provide a passage for a balloon and a closed position in which the pleating elements are close to or adjacent one another; each of said pleating elements including an elongate pleating blade and first and second pleating surfaces either side of the blade; wherein the first pleating surface of one folding element faces the second pleating surface of an adjacent pleating element; the method including the steps of: locating a cutting or scoring balloon to be folded into the apparatus; positioning the cutting or scoring elements adjacent the pleating blades of the apparatus; closing the pleating elements, thereby to cause the blades to push balloon wall material underneath the cutting or scoring elements; positioning the cutting or scoring elements in the gap between adjacent first and second pleating surfaces of adjacent pleating elements; and bringing the pleating elements to the closed position, thereby to pleat the balloon.

The step of positioning the cutting or scoring elements adjacent the pleating blades preferably includes the step of rotating the balloon relative to the pleating elements.

The first and second pleating surfaces are advantageously circumferentially curved, the first pleating surfaces being concave and the second pleating surfaces being convex; the method including the step of positioning the cutting or scoring elements on the side of the second pleating surfaces.

The apparatus and method provide a reliable system for pleating and wrapping a cutting or scoring balloon as taught herein.

BRIEF DESCRIPTION OF THE DRAWINGS

Embodiments of the present invention are described below, by way of example only, with reference to and as illustrated in the accompanying drawings, in which.

DESCRIPTION OF THE PREFERRED EMBODIMENTS

It is to be understood that the drawings are schematic and are not to scale.

Figure 1:
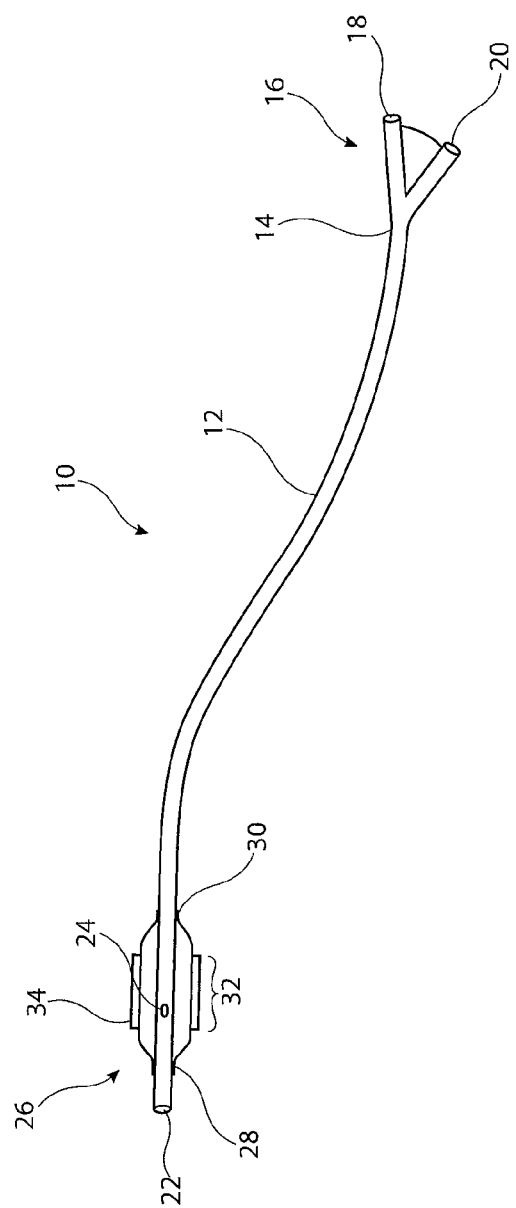
FIG. 1 is a schematic diagram of an example of cutting balloon catheter assembly.

Referring to FIG. 1, there is shown in schematic form an example of cutting or scoring balloon catheter assembly 10 which has, in the inflated state shown in FIG. 1, a generally conventional structure. More specifically, the assembly 10 includes a catheter 12 having a proximal end 14 coupled to a fitting 16, which in this example is a Y-fitting. The fitting 16 includes a first port 18 for the passage of a guide wire and a second port 20 for feeding inflation fluid into the catheter 12. The catheter 12 typically has at least two lumens passing therethrough, one from the first port 18 all the way to the distal end 22 of the catheter 12, for receiving a guide wire. The second lumen extends from the port 20 to an opening 24 proximate the distal end 22 of the catheter.

Attached to the distal end of the catheter is a cutting or scoring balloon 26, which at its ends 28 and 30 is fixed to the catheter 12 in fluid-tight manner. The balloon 26 also includes a generally cylindrical body portion 32, which has attached thereto or otherwise integral herewith a plurality of cutting or scoring elements 34 which extend generally in a longitudinal direction of the balloon 26, that is along the axis of the catheter 12. As will be apparent from FIG. 1, the opening 24 extends into the internal chamber of the balloon 26, thereby providing for the passage of inflation fluid into the balloon in order to inflate this. FIG. 1 shows the balloon 26 in its typically inflated form.

The balloon 26 is generally made of a thin-walled material, typically formed of one or more layers and may be compliant or non-compliant. A compliant balloon will continue to expand as the pressure of inflation fluid increases, whereas a non-compliant balloon will maintain a substantially constant inflated diameter over a range of operating pressures. The balloon wall may include one more strengthening elements such as strengthening wires or sleeves, preferably embedded within the thickness of the balloon wall.

The cutting or scoring elements 34 extend along the longitudinal axis of the balloon 26 but in other embodiments may extend at an angle to this, for example by being gently helically disposed.

The elements 34 may be sharp cutting blades of a hard material such as metal or metal alloy, a hard plastics or any other similar material. In other embodiments, the elements are less sharp, providing a scoring function, and may be formed as relatively blunt ribs extending along and radially out of the balloon wall. These ribs may be made of a variety of materials including metal or metal alloy, polymer, and in some embodiments the same material as that of the balloon wall. The cutting or scoring elements 34 provide relatively rigid members which act to tear or cut away stenosed material from a vessel wall.

For insertion into a patient's vasculature, the balloon 26 is deflated, pleated and wrapped around the catheter 12, and delivered through an introducer assembly. In the prior art, cutting or scoring balloons are typically wrapped loosely in an attempt to protect the balloon wall from the cutting or scoring elements and also in order to conceal the cutting or scoring elements until the balloon has been inflated. This, however, results in cutting or scoring balloons which are only loosely wrapped on the balloon catheter and which thus have a much greater delivery diameter. The teachings herein propose a different pleating and wrapping arrangement.

Figure 2:
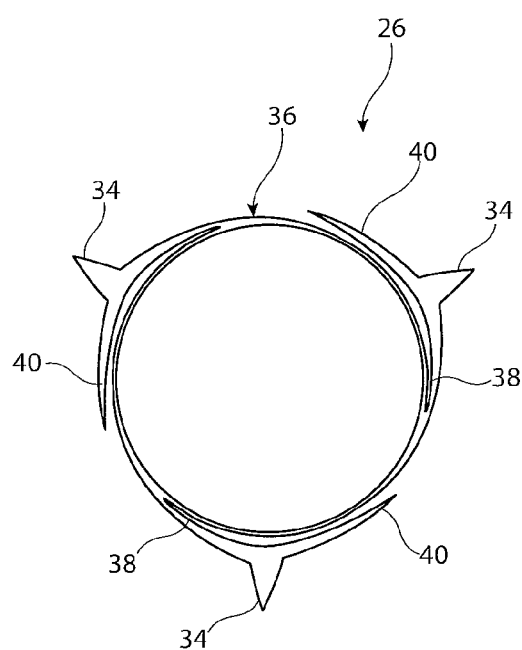
FIG. 2 is a transverse cross-sectional view of a preferred embodiment of wrapped cutting or scoring balloon.

Specifically, referring to FIG. 2, the balloon 26 of the preferred embodiment is shown in a wrapped configuration around the catheter 12, as it is configured for delivery through an introducer sheath or catheter of an introducer assembly. The balloon 26 includes a balloon wall 36 made of flexible material and which, when inflated, has a much larger diameter than the diameter of the catheter 12. As can be seen in FIG. 2, the balloon wall is pleated (or folded) and wrapped in such a manner that sections 38 of the balloon wall are pleated underneath the cutting or scoring elements 34, such that the cutting or scoring elements 34 are exposed even when the balloon is in its wrapped state. The balloon wall 36 may be pleated so as to leave overlying sections 40 extending in circumferentially opposite directions to the sections 38. However, the sections 40 extend circumferentially by an amount which is less than the spacing between adjacent cutting or scoring elements 34, such that the portions 40 do not extend over the cutting or scoring elements 34 but terminates short of these.

The overlying sections 40 may not be present in all the embodiments of cutting or scoring balloon 26. Specifically, in some embodiments all of the balloon material is pleated underneath the cutting or scoring elements, without there being any portion 40 or with only a minimal portion 40.

As can be seen in FIG. 2, the cutting or scoring balloon 26 is able to be tightly wrapped onto the catheter 12 as a result of the fact that the balloon wall 36 is pleated underneath the cutting or scoring elements 34. This provides a much tighter wrapped balloon compared to prior art arrangements and one in which the cutting or scoring elements 34 are exposed even when the balloon is in its fully deflated condition. This is considered advantageous, in being able to make use of the cutting or scoring elements 34 from the minimal wrapped balloon diameter all the way to its fully inflated diameter, as well as during the stages of intermediate inflation.

Figure 3:
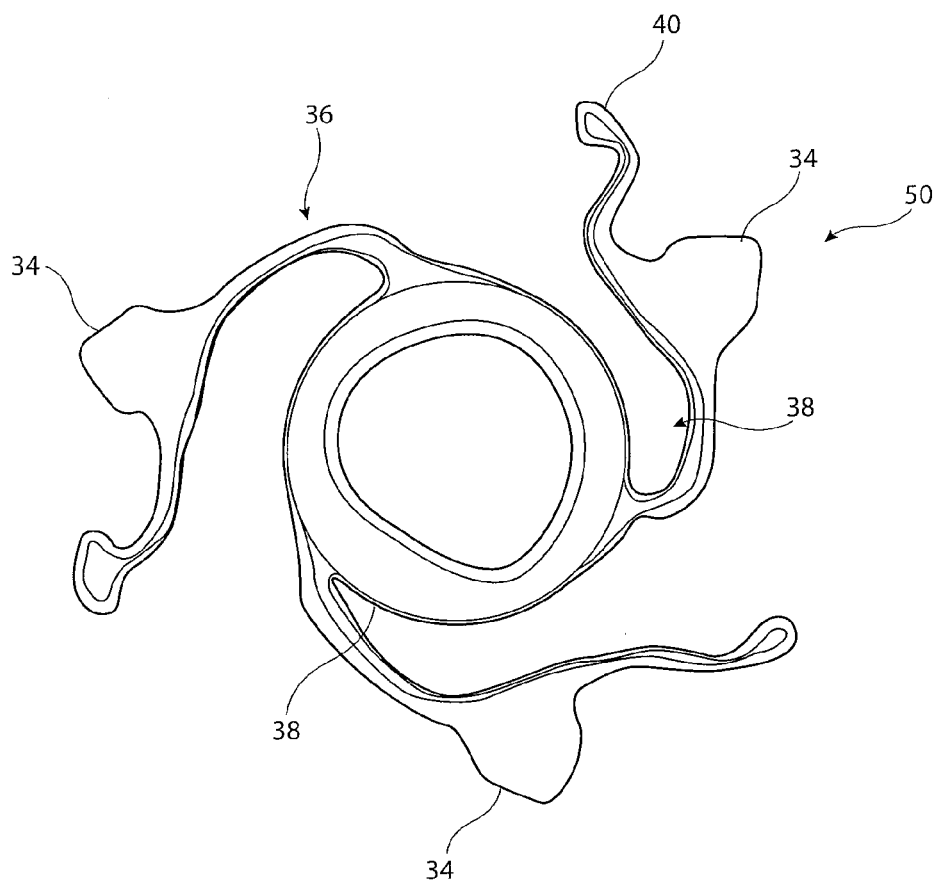
FIG. 3 is a transverse cross-sectional view of the cutting or scoring balloon of FIG. 2 after having been pleated by pleating apparatus.

FIG. 3 is a photograph of an actual example of scoring balloon in transverse cross-section. The balloon 50 is shown following pleating of the balloon by means of pleating apparatus described below and before it has been tightly wrapped by a wrapping device. FIG. 3 shows in clearer detail the pleated balloon wall 36, creating pleated regions 38 under the cutting or scoring elements 34.

With reference to the examples of the balloon shown in FIGS. 2 and 3, this is a scoring balloon in which the scoring elements 34 are ribs extending along the length of the balloon and are formed of the same material as the walls 36 of the balloon or of a material which is compatible therewith so as to form an integral and unitary structure with the balloon wall. This may be, for instance formed by extrusion through a suitably shaped dye. Other embodiments have cutting elements instead of the scoring elements 34. The cutting elements may be of a different material and attached to the outer surface of the balloon wall 36, for example, by means of adhesive and with or without a support base. Such cutting blades may have sharp blade elements and may be formed of metal or metal alloy for example.

Figure 4:
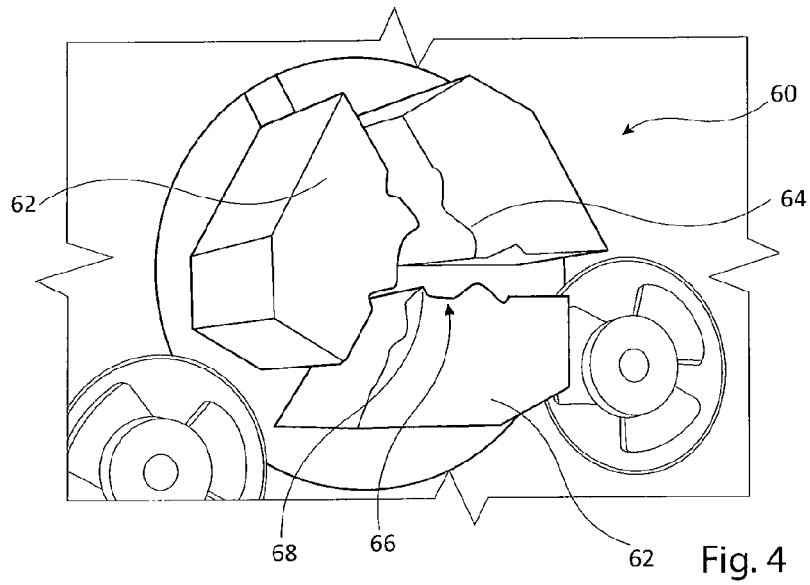
FIG. 4 is a view of part of a preferred embodiment of folding apparatus for pleating a balloon as shown in FIG. 3.

Referring now to FIG. 4, there is shown an embodiment of pleating machine and in particular of the pleating blade assembly 60 of such a machine. The pleating blade assembly 60 shown in FIGS. 4 to 6 has three blades 62 for pleating a balloon 26, 50 having three cutting or scoring elements 34. For balloons having a different number of cutting elements, the blade assembly 60 would have a different and equivalent number of pleating blades 62.

Each pleating blade 62 has a length at least as long as the body portion 32 of the balloon 26 and in general will be substantially longer than this so as to be able accommodate different sizes of balloon. Each pleating blade 62 includes an internal rounded surface 64 which extends along its length, as well as a side surface 66 which in the preferred embodiment also has a gentle curvature for facilitating pleating of the balloon, as will become apparent below.

The edge between the two surfaces 64 and 66 forms a pleating blade element 68 which, as a result of the curvature of surfaces 64 and 66, could be said to be have the form of a bird beak. As will be apparent in FIG. 4, the blade elements 68 have a common orientation, which can be described as being clockwise with reference to the view of FIG. 4. This common orientation will pleat the balloon 10, 50 into a plurality in this case three, equivalent pleats, all extending in the same rotational direction.

Figure 5:
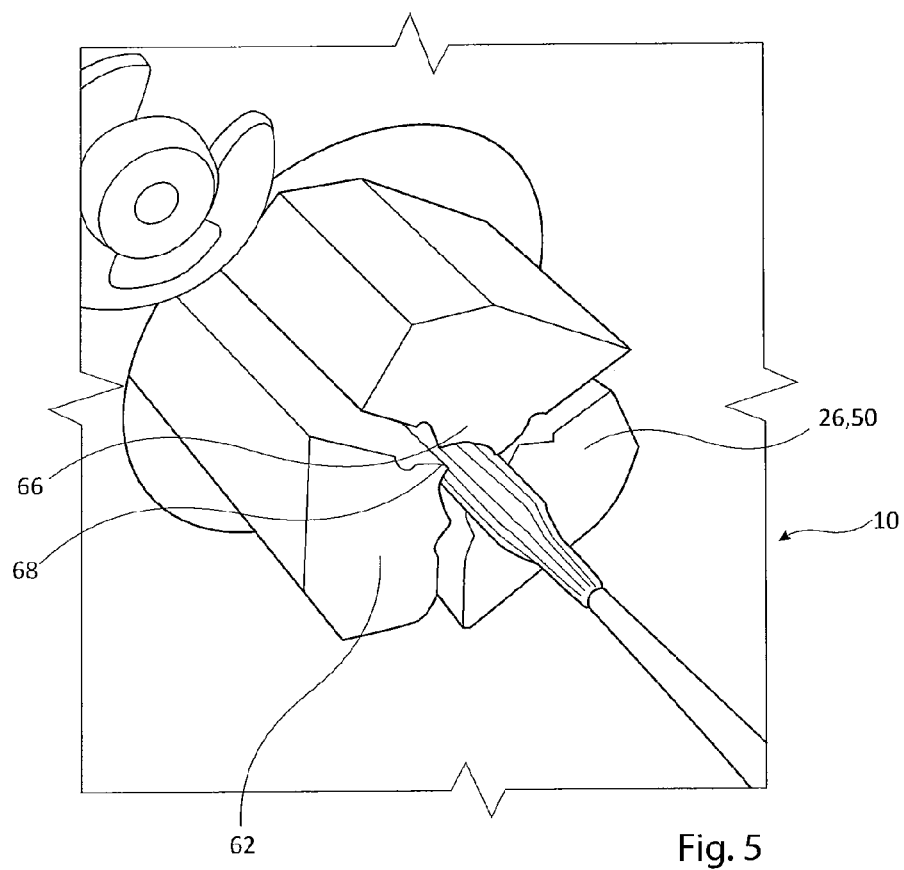
FIG. 5 is a view of the pleating apparatus of FIG. 4 showing a cutting balloon being positioned inside the pleating blades of the apparatus.
Figure 6:
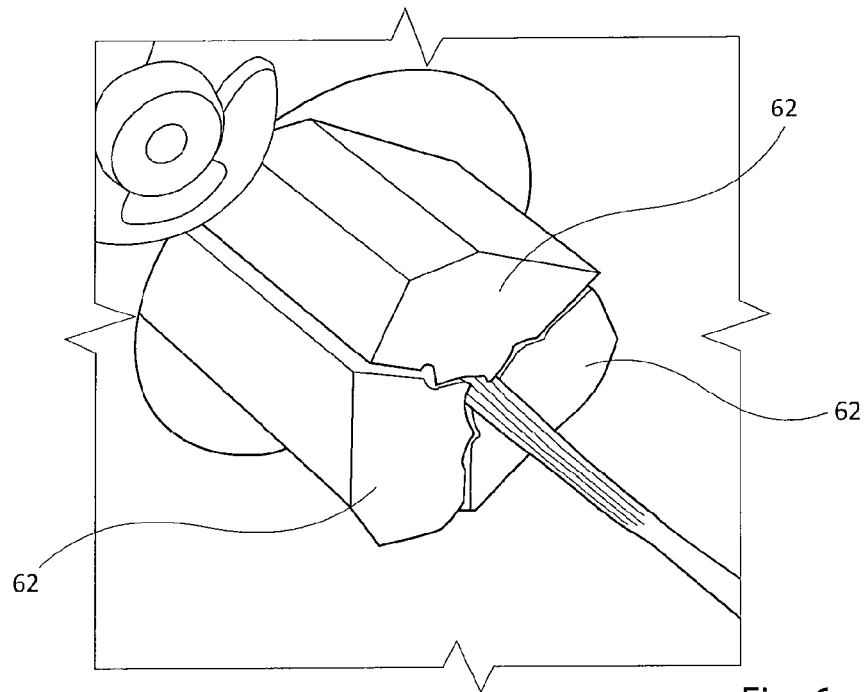
FIG. 6 shows the apparatus of FIG. 5 with the blades closing in on the balloon so as to pleat the balloon walls.

With reference to FIGS. 5 and 6, a balloon catheter is inserted into the gap between the pleating blades 62. The blades 62 are then gradually brought together so as to close the gap. At the appropriate closing, dependent upon the dimension of the balloon catheter when inserted into the device (at which point the balloon 26, 50 will be in an open configuration), the blade elements 68 will come into contact with the balloon 26,50. More particularly, the blade elements 68 are positioned preferably just alongside a respective cutting or scoring element 34, such that the blade 34 is on the side of each pleating blade 62 adjacent the curved side surface 66. As a result, blade elements 68 are able to press the balloon wall 36 underneath the cutting or scoring elements 34 as the pleating blades 62 are closed in further. This position of the balloon can be achieved by rotating the balloon catheter 10 until the cutting or scoring elements 34 come into position against a respective curved side surfaces 66.

Of course, if it is desired to retain a portion of balloon wall 36 alongside its associated cutting or scoring element prior to pleating, in the form shown FIGS. 2 and 3, the cutting or scoring elements 34 will not be positioned in abutment with a respective blade element 68 but will be slightly spaced therefrom radially.

Figure 7:
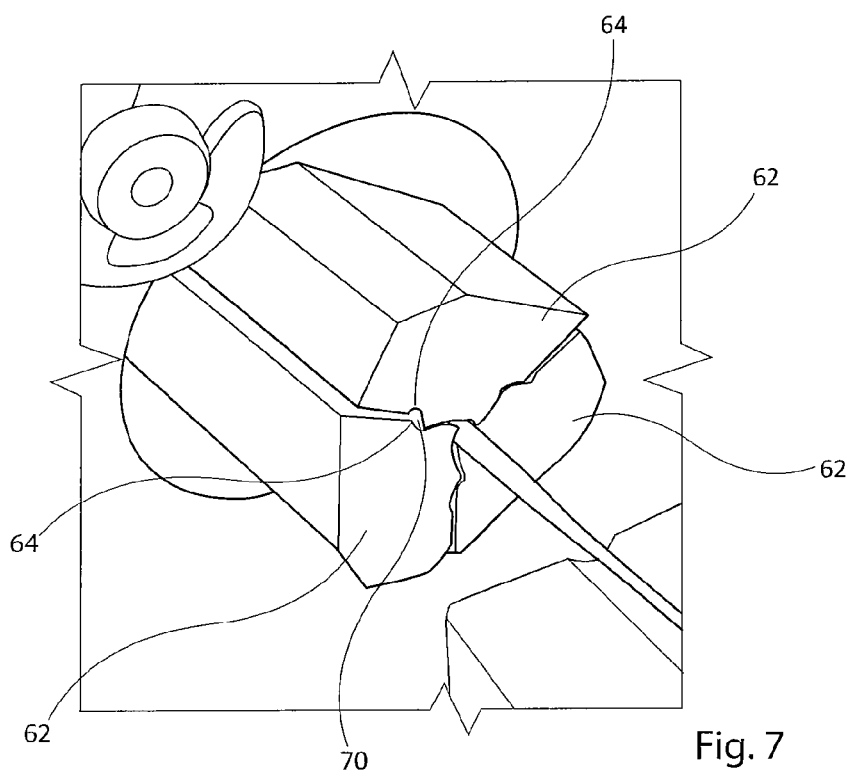
FIG. 7 shows the blades in a fully closed position with the balloon pleated.

As can be seen in FIG. 6, the folding blades 62 are further closed, thereby causing the balloon wall 36 to be pleated underneath the scoring or cutting elements 34. FIG. 7 shows the pleating blades 62 in their fully closed position. It can be seen that the inner surface 64 of one of the pleating blades 62 faces the side surface 66 of the adjacent pleating blade 62. However, there is a gap 70 between these two surfaces 64, 66 which accommodates on of the cutting or scoring elements 34. Thus, the pleating blade assembly 60 shown in FIGS. 4 to 7 is able to pleat balloons having cutting or scoring elements 24 already disposed thereon.

Figure 8:
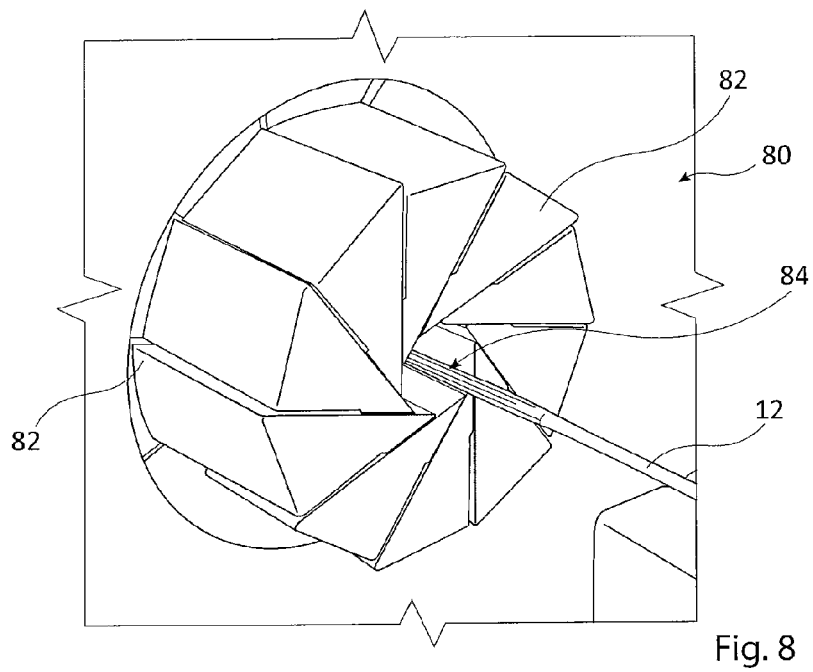
FIGS. 8 and 9 show an embodiment of wrapping apparatus for wrapping the pleated balloon tightly onto its carrier catheter.
Figure 9:
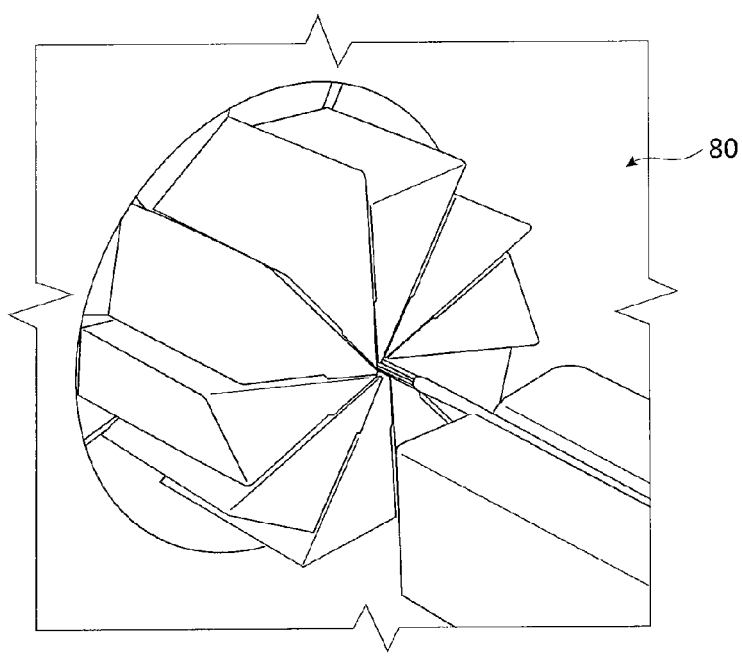

Referring now to FIGS. 8 and 9, these show a tool 80 for wrapping the pleated balloon. Specifically, after the balloon operation carried out by the pleating blade assembly 60 of FIGS. 4 to 7, the balloon will typically have a pleated shape as shown in FIG. 3. The wrapping tool 80 presses the flaps or wings of the pleated balloon around the catheter 12 so as to form a tightly wrapped structure as shown in FIG. 2.

The wrapping tool 80 includes, in this embodiment, a plurality of wedge elements 82 of elongate form which are arranged in an iris configuration able to close in so as to constrict the opening 84 therebetween. This can be seen in particular by a comparison of FIGS. 8 and 9.

The final wrapped balloon thus has a configuration in which the balloon wall 36 is pleated or folded underneath the cutting or scoring elements 34 and is tightly wrapped, as will be apparent in FIG. 2.

Having regard to FIGS. 4 to 9, it will be apparent that the cutting or scoring balloon 10, 50 is inflated so as to attain its open form, then fitted into the pleating blade assembly 60. Once in the assembly 60, the pleating blades 62 are, as necessary, brought close to the outside of the balloon wall 36 and the balloon 10, 50 then rotated so as to position its cutting or scoring elements adjacent the curved side surfaces 66 of the pleating assembly 60. The port 20 is then opened to allow fluid to escape from the balloon, as the pleating blades 62 are then moved in. This movement of the pleating blades 62 will pleat or fold the balloon wall 36 underneath the adjacent cutting or scoring elements 34, in the manner shown in FIG. 3. Once the pleating blades 62 have been fully closed and the balloon fully pleated, the balloon 10, 50 is withdrawn and then inserted into the wrapping assembly 80. The wedge elements 82 are progressively closed in iris manner, if necessary with suitable rotation of the pleated balloon 10, 50. Once the wrapping wedges 82 have been fully closed, the balloon 10, 50 will have the wrapped configuration shown in FIG. 2.

The wrapped balloon 10, 50 will typically be delivered via an introducer sheath of known form, save for the fact that the sheath can have a considerably smaller inner diameter compared to sheaths currently used for delivery of cutting or scoring balloons.

Once delivered and the carried sheath retracted, the balloon 10, 50 will have its cutting or scoring elements 34 exposed even with the balloon still in its fully wrapped configuration. Thus, the balloon 10, 50 can be used to cut through very tight stenoses. Inflation of the balloon 10, 50 will enable the balloon to continue cutting or scoring at the stenosis material, until the balloon reaches its inflated dimensions, which will be those of the vessel at its intended size.

It will be appreciated that described above are preferred embodiments of the present invention and that modifications may be made to these within the scope of the appended claims.

It is also to be understood that although the claims are set out in single dependent form, the features of the dependent claims are intended to be combined with one another as if they were cast in multiple dependent format.

The invention claimed is:

1. A pleated cutting or scoring balloon, the balloon including a flexible balloon wall having inner and outer surfaces, the balloon wall providing a balloon body portion extending along a longitudinal axis of the balloon and having a circumferential periphery; and a plurality of cutting or scoring elements integral with or attached to the outer surface of the balloon wall, said cutting or scoring elements extending substantially along said longitudinal axis and being spaced from one another along the circumferential periphery of the body portion; wherein a first portion of the balloon wall is wrapped directly underneath the cutting or scoring elements and a second portion of the balloon wall is wrapped over the first portion, the second portion thereby being exposed on the wrapped balloon, the cutting or scoring elements being located on the second portion and being exposed on the wrapped balloon such that at least part of the second portion is located on each side of the cutting or scoring elements; and wherein a centerline of the cutting or scoring elements extending through an apex of the cutting or scoring elements extends inward toward an axis of the wrapped balloon when the first and second portions are tightly wrapped.

2. A pleated cutting or scoring balloon according to claim 1, wherein the cutting or scoring elements are integral with the balloon wall.

3. A method of pleating a cutting or scoring balloon, the balloon including a flexible balloon wall having inner and outer surfaces, the balloon wall providing a balloon body portion extending along a longitudinal axis of the balloon and having a circumferential periphery; and a plurality of cutting or scoring elements on or attached to the outer surface of the balloon wall, said cutting or scoring elements extending substantially along said longitudinal axis and being spaced from one another along the circumferential periphery of the body portion; the method including the step of pleating the balloon wall such that a first portion of the balloon wall is wrapped directly underneath the cutting or scoring elements and a second portion of the balloon wall is wrapped over the first portion, the second portion thereby being exposed on the wrapped balloon, the cutting or scoring elements being located on the second portion and being exposed on the wrapped balloon such that at least part of the second portion is located on each side of the cutting or scoring elements; and wherein a centerline of the cutting or scoring elements extending through an apex of the cutting or scoring elements extends inward toward an axis of the wrapped balloon when the first and second portions are tightly wrapped.

4. A method according to claim 3, wherein the cutting or scoring elements are integral with the balloon wall.

5. A method of pleating a cutting or scoring balloon provided with a flexible balloon wall having inner and outer surfaces, the balloon wall providing a balloon body portion extending along a longitudinal axis of the balloon and having a circumferential periphery; and a plurality of cutting or scoring elements on or attached to the outer surface of the balloon wall, said cutting or scoring elements extending substantially along said longitudinal axis and being spaced from one another along the circumferential periphery of the body portion; the method using pleating apparatus including a plurality of pleating elements arranged in facing relationship with one another, said pleating elements being movable from an open position in which the blades provide a passage for a balloon and a closed position in which the pleating elements are close to or adjacent one another; each of said pleating elements including an elongate pleating blade and first and second pleating surfaces either side of the blade; wherein the first pleating surface of one folding element faces the second pleating surface of an adjacent pleating element; the method including the steps of:

locating a cutting or scoring balloon to be folded into the apparatus;

positioning the cutting or scoring elements adjacent the pleating blades of the apparatus;

closing the pleating elements, thereby to cause the blades to push balloon wall material underneath the cutting or scoring elements;

positioning the cutting or scoring elements in the gap between adjacent first and second pleating surfaces of adjacent pleating elements; and bringing the pleating elements to the closed position, thereby to pleat the balloon such that a first portion of the balloon wall is wrapped directly underneath the cutting or scoring elements and a second portion of the balloon wall is wrapped over the first portion, the second portion thereby being exposed on the wrapped balloon, the cutting or scoring elements being located on the second portion and being exposed on the wrapped balloon such that at least part of the second portion is located on each side of the cutting or scoring elements; and wherein a centerline of the cutting or scoring elements extending through an apex of the cutting or scoring elements extends inward toward an axis of the wrapped balloon when the first and second portions are tightly wrapped.

6. A method according to claim 5, wherein the step of positioning the cutting or scoring elements adjacent the pleating blades includes the step of rotating the balloon relative to the pleating elements.

7. A method according to claim 5, wherein the first and second pleating surfaces are circumferentially curved, the first pleating surfaces being concave and the second pleating surfaces being convex; the method including the step of positioning the cutting or scoring elements on the side of the second pleating surfaces.

8. A method according to claim 5, including the step of compressing the pleated balloon into a tightly wrapped condition.

9. A method according to claim 5, wherein the cutting or scoring elements are integral with the balloon wall.

* * * * *